United States Patent
Rickerd (10) Patent No.: US 7,377,909 B2
(45) Date of Patent: May 27, 2008

(54) CONNECTION ASSEMBLY FOR USE WITH SPLITTABLE SHEATH

(76) Inventor: Claude L Rickerd, 10649 Johnson Rd., Bloomington, MN (US) 55437

( * ) Notice: Subject to any disclaimer, the term of this patent is extended or adjusted under 35 U.S.C. 154(b) by 584 days.

(21) Appl. No.: 10/600,416

(22) Filed: Jun. 19, 2003

(65) Prior Publication Data
US 2004/0260243 A1 Dec. 23, 2004

(51) Int. Cl.
*A61M 5/178* (2006.01)
(52) U.S. Cl. .................................. 604/164.05
(58) Field of Classification Search .............. 604/161, 604/523, 241, 164.04–164.08, 533, 163, 604/534, 535, 246, 247
See application file for complete search history.

(56) References Cited

U.S. PATENT DOCUMENTS

| | | | |
|---|---|---|---|
| 4,214,594 A | 7/1980 | Little | |
| 4,436,519 A * | 3/1984 | O'Neill | 604/175 |
| 4,629,455 A * | 12/1986 | Kanno | 604/241 |
| 4,772,266 A * | 9/1988 | Groshong | 604/164.05 |
| 5,620,427 A | 4/1997 | Werschmidt et al. | |
| 5,843,031 A | 12/1998 | Hermann et al. | |
| 5,855,230 A | 1/1999 | Guala et al. | |
| 6,171,287 B1 | 1/2001 | Lynn et al. | |

* cited by examiner

*Primary Examiner*—Kevin C. Sirmons
*Assistant Examiner*—Catherine N. Witczak
(74) *Attorney, Agent, or Firm*—Heimbecher & Assoc., LLC (57) ABSTRACT

A connection system for connecting a hemostasis valve to a splittable sheath is disclosed. The connection system includes an adapter fitting having a shaft defining a lumen. The shaft has a proximal end and a distal end. On an external surface of the proximal end of the shaft, threading is provided for engagement with the hemostasis valve. A cannula portion defines the distal end of the shaft for interfacing with a splittable sheath. A wedge is disposed on an external surface of the cannula portion for interfacing with a weakened portion of the splittable sheath. A sliding connector is disposed about the shaft for engagement with the splittable sheath. Upon a first level of engagement between the sliding connector and the splittable sheath, a fluid-tight seal is created. Upon a second level of engagement between the sliding connector and the splittable sheath, the wedge initiates separation of the splittable sheath.

8 Claims, 5 Drawing Sheets

CONNECTION ASSEMBLY FOR USE WITH SPLITTABLE SHEATH

BACKGROUND OF INVENTION a. Field of the Invention

This invention relates generally to the field of medical instruments used for intra-arterial and intravenous introduction of instruments and more specifically to a connection assembly for creating a fluid seal connection between such medical instruments.

b. Background Art

There are a number of medical procedures which require the introduction of medical instruments into arteries and veins. In one such procedure, known as the Seldinger procedure, a surgical opening is made in a vein or artery with a needle. A guide wire is then inserted through the lumen of the needle into the vein or artery. The needle is withdrawn, leaving the guide wire in place. A dilator is then inserted over the guide wire inside an associated sheath. The dilator and guidewire are removed once the sheath is in place. At this point, various types of catheters or leads may be inserted into the vessel within the lumen of the sheath using the sheath as a conduit to prevent damage to the vessel wall.

In certain medical procedures, for example, where a pacemaker lead is inserted into a patient, a sheath is normally used to guide the pacemaker lead to the appropriate location. Before the pacemaker lead is permanently secured in place and attached to a pacemaker, the sheath must be removed. Because of the size of its lumen, the sheath cannot simply slip over the exterior end of the pacemaker lead as that end of the lead contains a connector coupling for connection to the pacemaker.

Accordingly, there have been disclosed a number of splittable sheaths for use in the introduction of pacemaker lead. These sheaths can be split in half while still surrounding the pacemaker lead. In this use, once the pacemaker lead is in place, the sheath is longitudinally severed and removed from the pacemaker lead. For example, U.S. Pat. No. 4,983,168 discloses such a layered, peel-away hollow sheath, wherein the sheath wall is comprised of at least two layers, an inside cylindrical layer and an outside layer comprising two semi-cylindrical segments defining opposed axially-directed slits or slots therebetween, which comprise tear lines. U.S. Pat. No. 4,596,559 discloses a tear away sheath for use with a disposable introducer set in conjunction with a catheter. U.S. Pat. No. Re. 31,855 discloses a sheath that has an internal molecular orientation which tears easily in a lengthwise direction and with great difficulty in a crosswise or oblique direction. See also U.S. Pat. No. 4,581,025. Longitudinally scored or perforated sheaths are disclosed in U.S. Pat. Nos. 4,166,469; 4,243,050; 4,345,606; and 4,451,256.

Several problems may be encountered during the use of these splittable sheaths. For example, during the introduction of a pacemaker lead, a significant amount of bleeding may occur at the operation site, depending upon the blood pressure present in the vessel. Once the sheath is in place within a vessel, it provides a passageway for the free flow of blood away from the operation site. Further, because of this flow of blood, clotting may occur if the sheath remains in position for an extended period of time. These clots may cause emboli which may pass to the lung and have a detrimental impact on the patient. The use of sheaths may also provide a passageway for the introduction of air into the vessel. The inadvertent introduction of air into the blood system can cause air emboli in the patient that may have negative effects. Because of such problems, splittable sheaths are often removed from the theater of operation as soon as possible, even if it would be preferable to maintain them in position for a longer period of time. Such hurried procedures can result in errors or medical complications.

One method for restricting the flow of blood out of a sheath while a pacemaker lead is being introduced is for the physician to place his thumb over the exposed end of the sheath or to squeeze or pinch the exposed end of the sheath between his thumb and forefinger. However, neither of these methods for reducing the undesired flow of blood and air through the sheath is desirable, because the opportunity for loss of blood and introduction of air is still present. In addition, the structure of these sheaths still requires the surgeon to hold onto it while it is in place in the vessel, thereby limiting the surgeon's ability to perform other medical procedures at the same time. Moreover, squeezing the exposed end of the sheath can deform or even break the sheath, making lead insertion difficult and increasing the likelihood of damage to the lead as it passes through the sheath. Further, even when holding the end of the sheath or pinching the sheath, the flow of blood out of the sheath is not entirely stopped.

For these reasons, a hemostasis valve is often used in conjunction with a sheath to limit blood flow during the introduction of guide wires, catheters, pacemaker leads and other similar medical devices into the heart. This use of a hemostasis valve may, however, cause some issues. For example, because the exterior end of pacemaker leads is larger than the opening in conventional hemostasis valves, it is not possible for pacemaker leads to pass through these conventional hemostasis valves. In many cases the hemostasis valve is designed for use with a specific size of a catheter. Such hemostasis valves have been disclosed, for example, in U.S. Pat. Nos. 5,092,857 and 4,909,798. Another solution to this problem has been to provide splittable hemostasis valves integrally formed with splittable sheaths for the introduction of pacemaker leads as disclosed, for example, in U.S. Pat. Nos. 5,312,355 and 5,125,904. Similarly, splittable hemostasis valves that are not integral with a sheath, but merely connected thereto, may be used (see, for example, U.S. Pat. No. 6,083,207). A further solution to the problem has been to provide a "universal" hemostasis valve, wherein the valve assembly is designed to accommodate leads and catheters of a wide range of diameters.

A wide variety of circumstances can dictate which type of hemostasis valve is chosen for a particular application or in a particular situation. For example, the physician may want to delay introduction of a hemostasis valve onto a sheath until after the sheath is in position. This would suggest that an integral hemostasis valve and sheath is not desirable. In some circumstances, multiple leads or catheters of various diameters may need to be used. In these instances, particularly sized hemostasis valves would not be preferred. In other circumstances, the hemostasis valve may need to be removed during the operation, or perhaps removed and replaced several different times while the sheath remains in place. Such use might counsel against a splittable hemostasis valve that may be prone to leakage once split. Further, it is sometimes necessary to remove the hemostasis valve from the operating theater at a time when the sheath is still in use.

When the particular choice is made to use a non-splitting hemostasis valve, a further problem may arise that remains unaddressed by prior designs. Once introduced into the body intravascularly, leads are often placed in particular and sensitive positions and the intention is for the lead to remain in place. This is particularly true in the case of pacemaker leads that are imbedded in precise locations in the heart muscle to achieve particular results. The problem suggested occurs when attempting to remove the sheath from the patient's blood vessel and from about the lead. In some instances it may be difficult to initiate the tearing of the splittable sheath to remove it. Some amount of force must be applied both distally and radially with respect to the lumen diameter of the sheath in order to pull the two halves of the sheath apart. The initial force required to cause the sheath to begin separation at the proximal end is generally greater than the continuing force required to split the length of the sheath as it is removed from the patient's blood vessel. Sometimes the hemostasis valve is attached to the sheath with a Luer lock interface. When applying this initial force, the lead may be unintentionally moved and either dislodge from or otherwise become misplaced about the heart muscle.

The information included in this Background section of the specification, including any references cited herein and any description or discussion thereof, is included for technical reference purposes only and, but is not to be regarded as subject matter by which the scope of the invention is to be bound.

SUMMARY OF INVENTION

The present invention is fundamentally a connection system for connecting a hemostasis valve to a sheath. In one embodiment, the hemostasis valve has a first engagement means disposed on a distal end thereof. The splittable sheath has a second engagement means disposed on a proximal end thereof. An adapter fitting is disposed between the hemostasis valve and the splittable sheath. The adapter fitting is defined by a shaft defining a lumen, wherein the shaft has a proximal end and a distal end. A third engagement means is provided on an eternal surface of the proximal end of the shaft for engagement with the first engagement means of the hemostasis valve. A cannula portion forms the distal end of the shaft for interfacing with a lumen of the splittable sheath adapted for receiving the cannula portion. The cannula portion is further formed with at least one wedge disposed on an external surface of the cannula portion for interfacing with a weakened portion of the splittable sheath. Finally, a sliding connector disposed about the shaft of the adapter fitting, the sliding connector defining an opening through which the proximal end of the shaft protrudes, the sliding connector further comprising a fourth engagement means for engagement with the second engagement means of the splittable sheath.

In another embodiment of the invention, an adapter fitting is disclosed for use in a connection system for connecting a hemostatis valve to a splittable sheath. The adapter fitting is based upon a shaft defining a lumen. The shaft has a proximal end and a distal end. On an external surface of the proximal end of the shaft, threading is provided for engagement with a hemostasis valve. A cannula portion defines the distal end of the shaft for interfacing with a splittable sheath. A wedge is disposed on an external surface of the cannula portion for interfacing with a weakened portion of the splittable sheath. A sliding connector is then disposed about the shaft and is provided for engagement with the splittable sheath.

The benefit of using the connection system of the present invention is that the adapter fitting provides both a structure for creating a seal between the hemostasis valve and the splittable sheath, and also a structure for initiating the separation of the splittable sheath without initially requiring the physician to impart a tearing force on the splittable sheath. Upon a first level of engagement between the sliding connector and the splittable sheath, a fluid-tight seal is created. Upon a second level of engagement between the sliding connector and the splittable sheath, the wedge on the cannula portion of the adapter fitting initiates separation of the splittable sheath.

Other features, utilities, and advantages of various embodiments of the invention will be apparent from the following more particular description of embodiments of the invention as illustrated in the accompanying drawings and defined in the appended claims.

DETAILED DESCRIPTION OF PREFERRED EMBODIMENTS

The following disclosure of the invention describes a connection system for connecting a hemostasis valve to a splittable sheath. An intermediate fitting is provided between the hemostasis valve and the sheath to connect one component to the other. The adapter fitting may have a frustum-shaped cannula portion for interfacing with the lumen of the sheath. The cannula of the adapter fitting may further have a wedge disposed to engage the sheath. A sliding or free spinning connector can be tightened to a first level of engagement with an opposing mating component of the sheath to create a fluid tight seal between the level fitting and the sheath. The sliding connector can also be tightened to a second level of engagement with the mating component of the sheath to drive a wedge on the cannula portion of the adapter fitting into the sheath to initiate splitting of the sheath.

Figure 1:
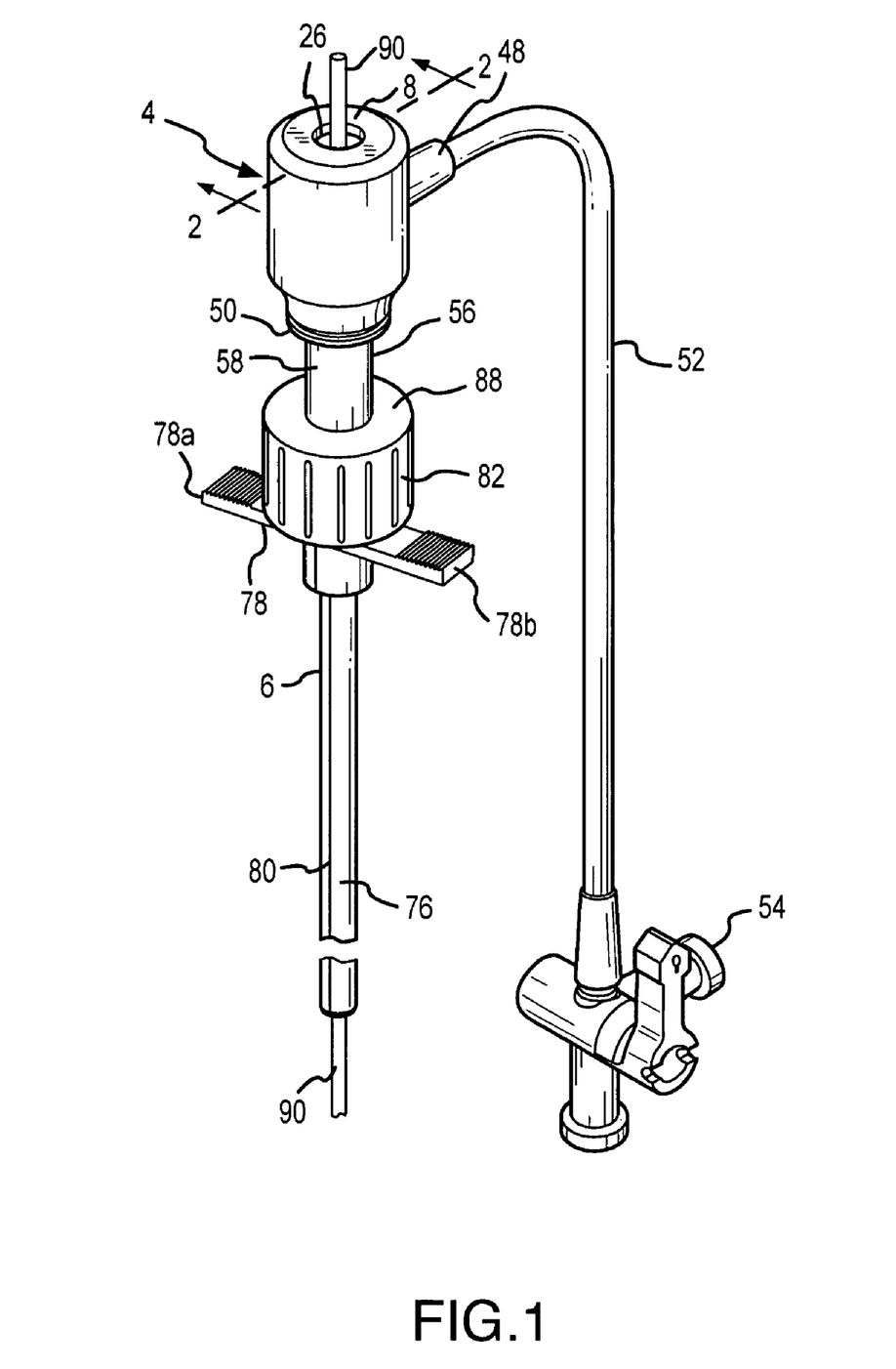
FIG. 1 is an isometric view of a connection assembly according to one embodiment of the invention joining a hemostatis valve to a splittable sheath.
Figure 2:
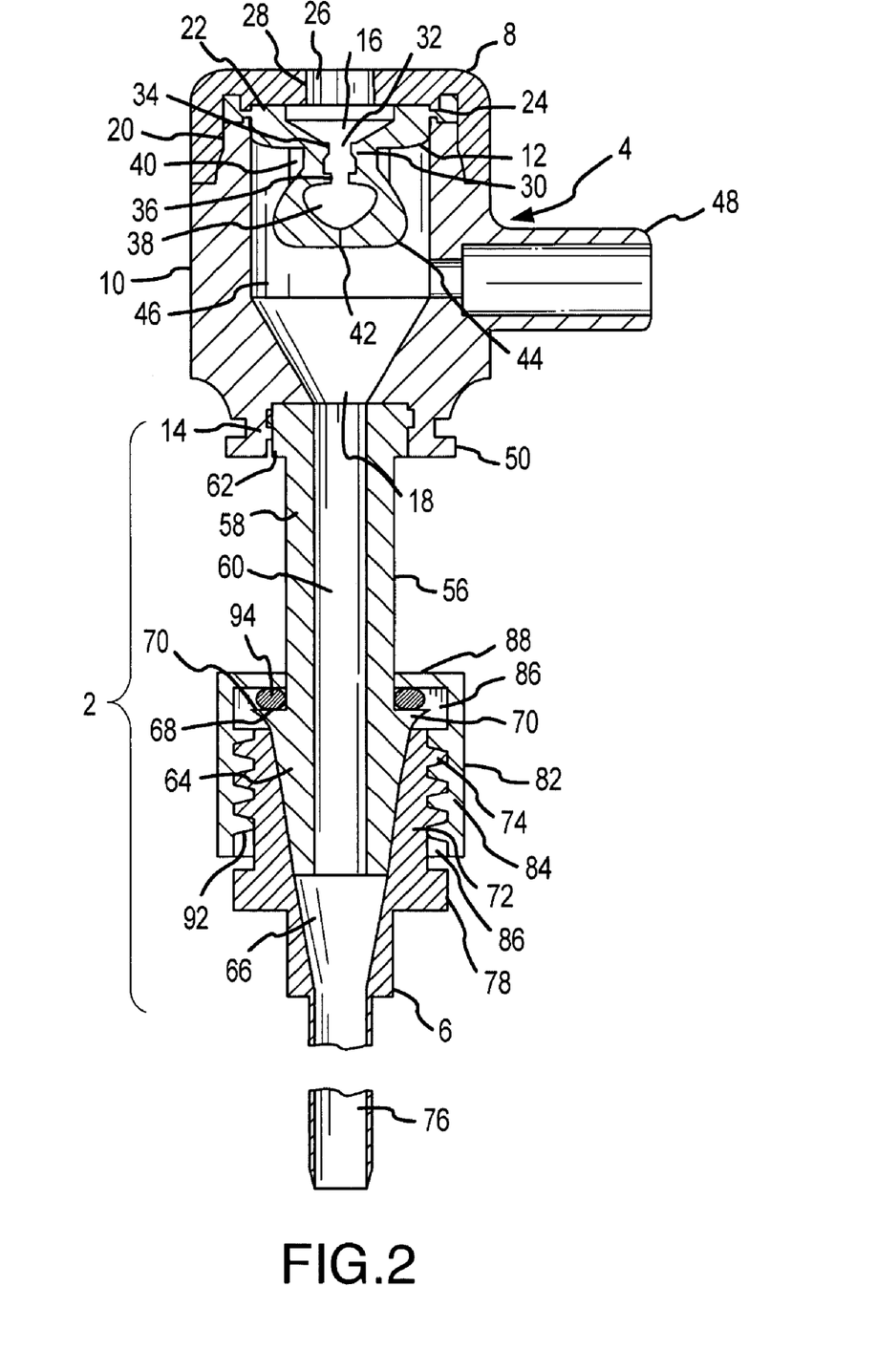
FIG. 2 is a cross section of the connection assembly, hemostasis valve, and splittable sheath as indicated in FIG. 1.
Figure 3:
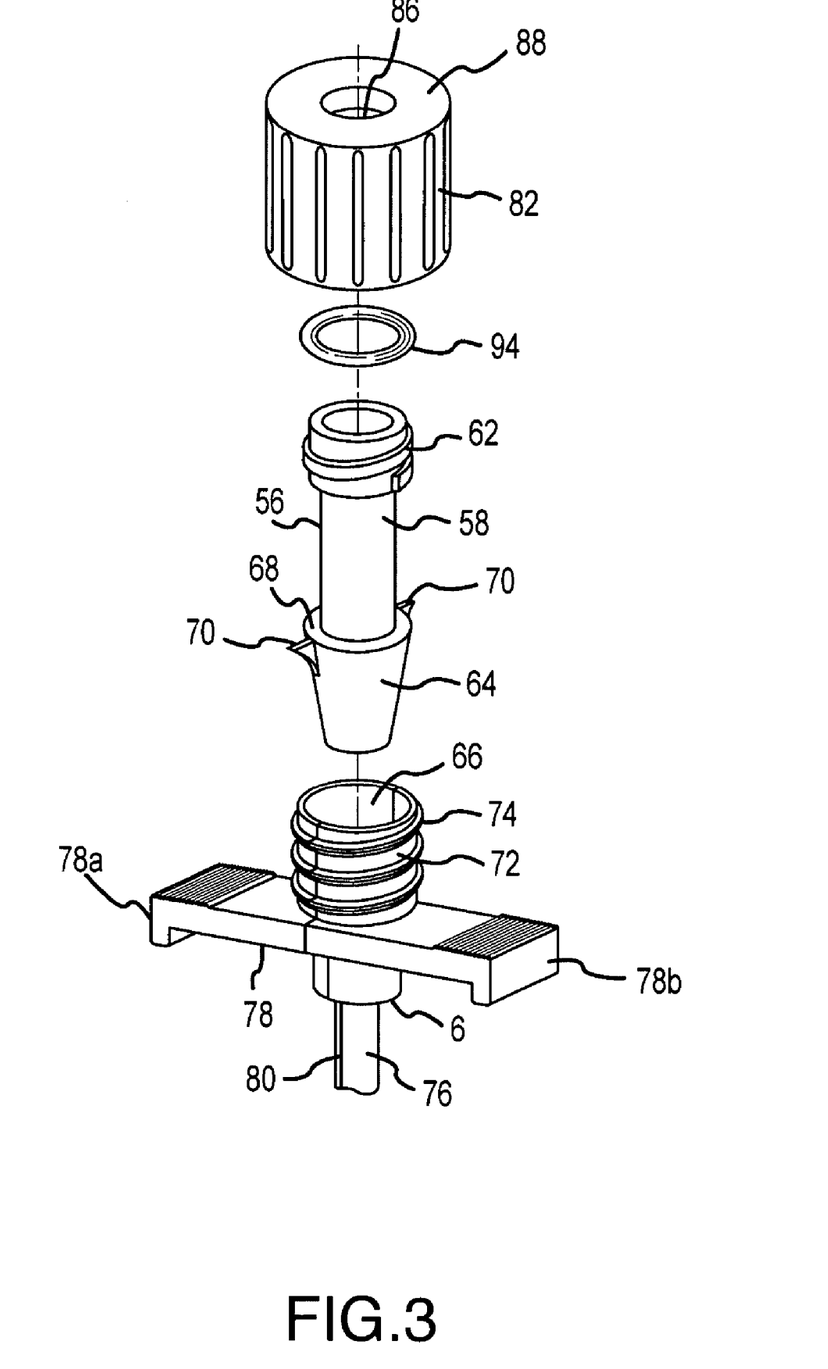
FIG. 3 is an exploded isometric view showing the individual components of the connection assembly indicated on FIG. 1.

One embodiment of a connection assembly 2 for use in conjunction with a separate hemostasis valve 4 and splittable sheath 6 combination according to the present invention is depicted in FIGS. 1-3. The connection assembly 2 is primarily composed of an adapter fitting 56 and a sliding connector 80. In FIGS. 1 and 2 the connection assembly 2 is shown fastened, connecting the hemostasis valve 4 via the adapter fitting 56 to the splittable sheath 6. FIG. 2 is a cross section of FIG. 1. In FIG. 3 the components of the connection assembly 2 are shown in an exploded format.

The upper part of FIGS. 1 and 2 depict the features of an exemplary hemostasis valve 4. The hemostasis valve 4 is formed from four major parts: a cap 8, a valve housing 10, a valve assembly 12, and an engagement portion 14. The cap 8 is attached to the top of the longitudinally extended valve housing 10. The valve housing 12 has first and second opposing open ends 16, 18 to permit insertion of a catheter dilator, guidewire, lead 90, or other instrument into and out of the interior of the valve housing 10. Hereinafter, the term "lead" will be used to refer generally to all instruments, including guidewires, lead, dilators, and catheters that may be inserted into the hemostasis valve 4 and sheath 6. The cap 8 and the valve housing 10 are formed from a relatively hard plastic, such as polycarbonate. The cap 8 may be secured to the valve housing 10, for example, by gluing, heat sealing, ultrasonic bonding, and by mechanically attaching to the valve housing, for example, threads, clips, or, as shown in the drawings, a snap fitting 20. The cap 8 and the valve housing 10 are first molded with respective interference fits and then may additionally be ultrasonically bonded together.

The hemostasis valve 4 also includes the valve assembly 12, which is formed from a pliant, resilient rubber such as silicone rubber or latex rubber having a durometer range of about 20-60 (Shore A), and which can be shaped to readily allow the passage of various sized leads 90. The valve assembly 12 may be of a one piece valve construction, although a two piece, moldable valve assembly may also be used.

The hemostasis valve 4 also contains an engagement portion 14, which may be formed integrally with the hemostasis valve 4. The engagement portion 14 extends distally from the valve housing 10 and cooperates to provide an exit through open end 18 from the interior of the valve housing 10. The engagement portion 14 further includes an engagement structure for interfacing with the adapter fitting 56. This engagement structure may be, for example, a male Luer fitting with internal threading.

As shown in FIGS. 1 and 2, the valve assembly 12, the cap 8, and the valve housing 10 are joined together by inserting the valve assembly 12 into the cap 8 such that the uppermost edge 22 of the valve assembly 12 is fully inserted within the cap 8 and rests against a rib 24, which is preferably circular in nature. The cap 8 with the valve assembly 12 in position is then placed on top of the valve housing 10. The valve assembly 12 is inserted inside the valve housing 10, and downward pressure is applied to the cap 8 along with ultrasonic energy to bond the cap 8 to the valve housing 10. With the cap 8 and valve housing 10 engaged, downward pressure on the cap 8 is maintained causing compression of the uppermost edge of the valve assembly 12 by the rib 24 which serves to hold the valve assembly 12 in place within the valve housing 10.

The cap 8 is provided with a first opening 26 at the top, which can receive lead 90 that is inserted within the hemostasis valve 4 for purposes of introduction into body vessels. An exemplary valve assembly 12 has a conical receiving area 28 that tapers into a sealing neck 30 having a neck opening 32. Taken together the conical receiving area 28 and neck opening 32 provide for easy insertion of a lead 90 into the valve assembly 12 and through the neck opening 32. The sealing neck 30 may have a first narrowed portion 34 in communication with the conical receiving area 28, a second narrowed portion 36 in communication with a sealing chamber 38, and a broadened portion 40 between these first and second narrowed portions 34, 36.

The diameter of the opening of the first and second narrowed portions 34, 36 is slightly less than the diameter of a conventional lead 90 that will pass through this sealing neck 30. Preferably, the first narrowed portion 34 is slightly smaller than the second narrowed portion 36, although the first narrowed portion 34 may be larger than or the same diameter as the second narrowed portion 36. By reducing the amount of inner surface area of the sealing neck 30, which contacts a lead 90 as it passes through the passageway of the sealing neck 30, resistance to the movement of the lead 90 through the sealing neck 30 is also reduced. Notwithstanding this reduced resistance, a good seal is still created against bleeding because of the presence of the first and second narrowed portions 34, 36 of the sealing neck 30 which continue to press against the guidewire as it passes through the hemostasis valve 4. The amount of the resistance to the movement of the lead 90 through the hemostasis valve 4 is directly related to the amount of material in the sealing neck 30 that contacts the lead 90 as it passes through the seal. By reducing the amount of this seal material to a minimum while at the same time retaining hemostasis around the lead 90 while passing through the sealing neck 30, good "feel" is provided while at the same time minimizing hemodynamic pressure dampening.

Communicating with the conical receiving area 28 and the neck opening 32 is the sealing chamber 38, which may be of any convenient shape, although preferably, it is semi-spherical or flattened spherical in shape. The interior diameter of the sealing chamber 38 is preferably the same as the largest outside diameter of any lead 90 that will be employed with the hemostasis valve 4. The diameter of the second narrowed portion 36 of the sealing neck 30, which is closest to the sealing chamber 38, may be slightly smaller than that of any lead 90 that will be employed so as to provide for sealing against the reverse flow of blood which may enter into the sealing chamber 38 while a lead 90 is in place in the hemostasis valve 4.

In order to provide support for the valve assembly 12 when a lead 90 is inserted through the sealing neck 30, support shoulders 40 may be located on the outside of the valve assembly 12 where the conical receiving area 28 tapers into the sealing neck 30 as shown in FIGS. 1 and 2. The support shoulders 40 do not extend outward beyond the widest portion of the sealing chamber 38 or downward around the outside surface of the sealing chamber 38 to increase the overall diameter of the valve assembly 12. Specifically, the support shoulders 40 do not increase the outside diameter of that portion of the valve assembly 12 containing the sealing chamber 30. Also, the support shoulders 40 do not extend downward beyond the widest portion of the outside of the sealing chamber 30, thus avoiding undue expansion of the neck opening 32 against the side walls of the valve housing 10 upon insertion of a large diameter lead 90. As a result, when a lead 90 is inserted through the neck opening 32, the sealing neck 30 will not unduly bulge out and come into contact with the walls of the valve housing 10. The support shoulders 40 also prevent the valve assembly 12 from extending excessively downward toward the second open end 18 of the valve housing 10 and, importantly, provide support for the seal on insertion and removal of leads 90 through the valve.

A single slit 42 in the valve assembly 12 creates opposing sealing lips 44 that are forced open by a lead 90 inserted into the body of the hemostasis valve 4. The spacial geometry of the walls of the semi-spherical sealing chamber 38 strongly force opposing sealing lips 44 into a normally closed position and hold them in that position to prevent an external reverse flow of blood. Likewise, when the sealing lips 44 are opened after a lead 90 is inserted, the opposing forces of the sealing neck 30 seal around the lead 90 and halt the reverse flow of blood.

The valve housing 10 is longitudinally extended to form a valve chamber 46. The distal portion of the valve chamber 46 may be tapered to constrain the lead 90 to ultimately guide it into the sheath 6. The first and second open ends 16, 18 of the valve housing 10 allow a lead 90 to be inserted through the valve chamber 46. Access to the interior of the valve chamber 46 may also be provided through a port 48 to which is attached tubing 52 and a fitting, for example, a stop cock 54, to permit insertion or withdrawal of fluids from the valve chamber 46 during use. The valve housing 10 of the hemostasis valve 4 may also be provided with a suture ring 50 to allow temporary attachment of the engagement portion 14 of the hemostasis valve 4 directly to a patient's body to provide stabilization of the hemostasis valve 4.

Figure 4:
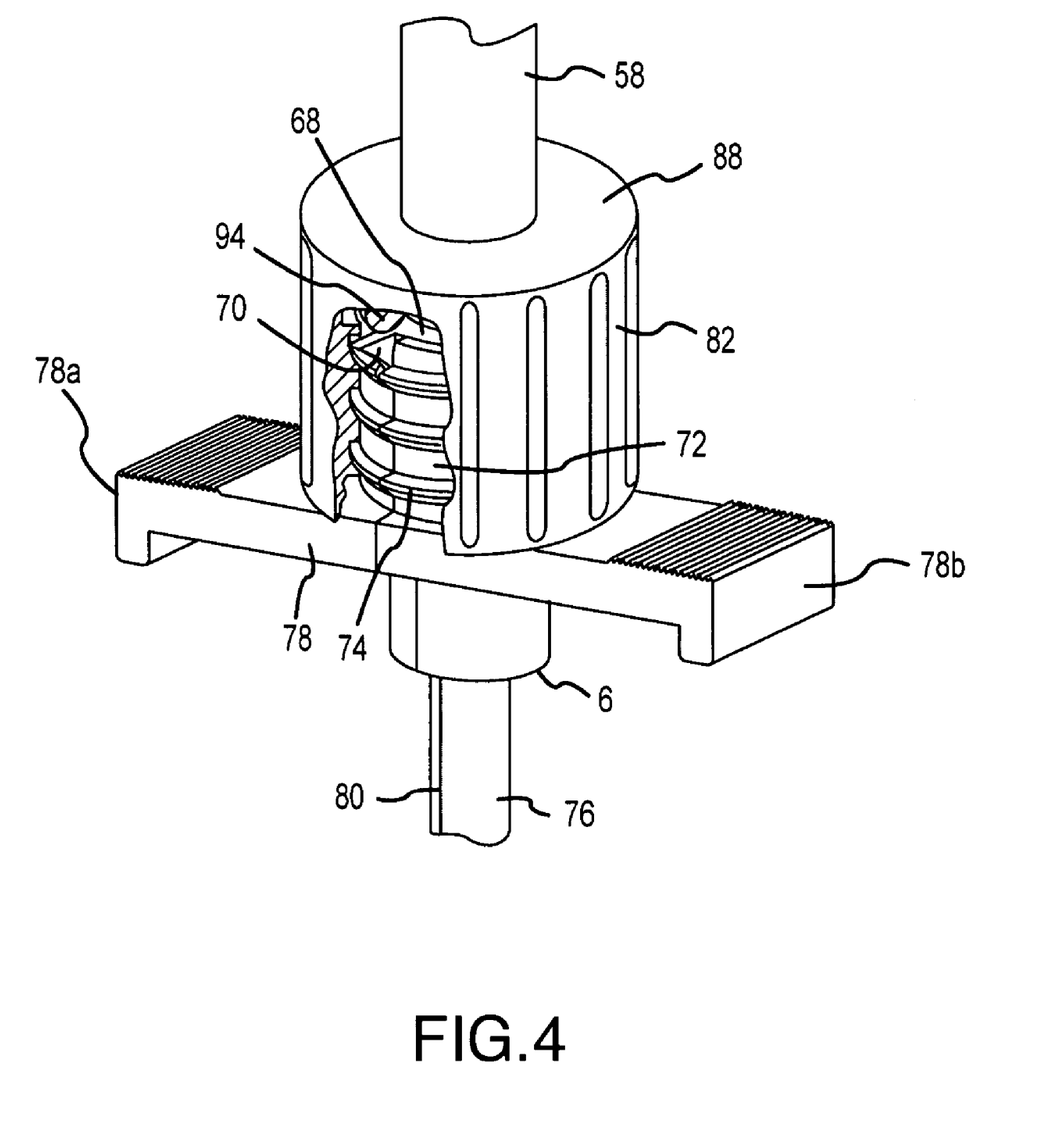
FIG. 4 is a detailed isometric view of the connection assembly of FIG. 1 with a partial cutaway revealing the wedge initiating separation of the sheath.

As shown in FIGS. 1, 2, and 4, the engagement portion 14 of the hemostasis valve 4 interfaces with the adapter fitting 56. The adapter fitting 56 is generally a shaft 58 defining a lumen 60 of constant diameter that is at least as large in diameter as the proximal opening in the hemostasis valve 4. The constant diameter of the lumen 60 of the adapter fitting 56 ensures adequate clearance for insertion and withdrawal of any leads 90. The proximal end of the shaft 6 may have an engagement structure 62, for example, a female Luer fitting, for connecting with the engagement portion 14 of the hemostasis valve 4. For example, the engagement structure 62 may be external threading on the shaft 58 for engagement in a male Luer fitting on the hemostasis valve 4. The distal end of the shaft 58 may be formed as a frustrum-shaped cannula portion 64 that is tapered at the distal end for insertion into a symmetrically tapered lumen 66 in the proximal end of the splittable sheath 6. The cannula portion 64 may further have an annular shelf 68 defined by the larger diameter of the frustrum. The diameter of the frustrum of the cannula portion 64 at this point is larger than the diameter of the shaft 58 extending proximally toward the hemostasis valve 4, thus forming the annular shelf 68. A wedge 70 may be positioned on the outer surface of the cannula portion 64 adjacent to the larger diameter of the frustrum.

A sheath 6 is provided as part of the connection system 2 and is adapted at its proximal end to interface with the adapter fitting 56. In one embodiment, as shown in FIGS. 1-5, the sheath 6 may have a nipple 72 on the proximal end. The nipple 72 is generally an annular wall defining a mating lumen 66. The nipple lumen 66 may be tapered distally at the same grade of decreasing diameter as the outer surface of the tapered cannula portion 64 of the adapter fitting 56. With these opposing tapered structures, the cannula portion 64 of the adapter fitting 56 may be seated within and interface with the nipple lumen 66. The nipple 72 is further formed with a continuous annular ridge 74 extending in a spiral circumferentially about the outer surface of the nipple 72 to form a male threaded engagement.

The sheath 6 may be a generally elongated, substantially cylindrical tube 76 having a handle 78 fixed to its proximal end. It may be formed by extrusion of any suitable plastic material, preferably a polyethylene or tetrafloroethylene plastic such as Pebax® (AUTOFINA Chemicals, Inc., Philadelphia, Pa.), wherein the plastic is compatible with body fluids, particularly blood. As shown in FIGS. 1, 3, and 4, the sheath 6 may also be designed to split in half and tear apart from about an indwelling lead 90. The tube 76 has a proximal end and a distal end and mechanically formed, longitudinally extending zones of reduced thickness defined by internally scored, longitudinally shallow grooves, or indentations 80 running the length of the tube. The handle 78 preferably includes a pair of handle members 78a, 78b projecting perpendicularly outward from the cylindrically shaped tube 76. Upon pressure being placed against the top of the handle members 78a, 78b and outward radial force of pulling, the tube 76 splits for removal from about the lead 90 previously inserted within.

In the embodiment of FIGS. 1-5, a sliding connector 82 is disposed about the outer surface of the adapter fitting 56. In general, the sliding connector 82 comprises an annular wall 84 defining a lumen 86 disposed about the outer surface of the shaft 58 of the adapter fitting 56. An annular lip 88 extends radially inward reducing the diameter of the connector lumen 86 at the proximal end of the sliding connector 82. The annular lip 88 is positioned on the proximal side of the cannula portion 64 of the adapter fitting 56 for engagement with the proximal side of the annular shelf 68 of the frustrum, thereby retaining the sliding connector 82 about the shaft 58, as shown in FIG. 2. The sliding connector 82 may slide proximally and distally along the shaft 58 of the adapter fitting 56 within the bounds allowed distally by the retention of the annular shelf 68.

Figure 5:
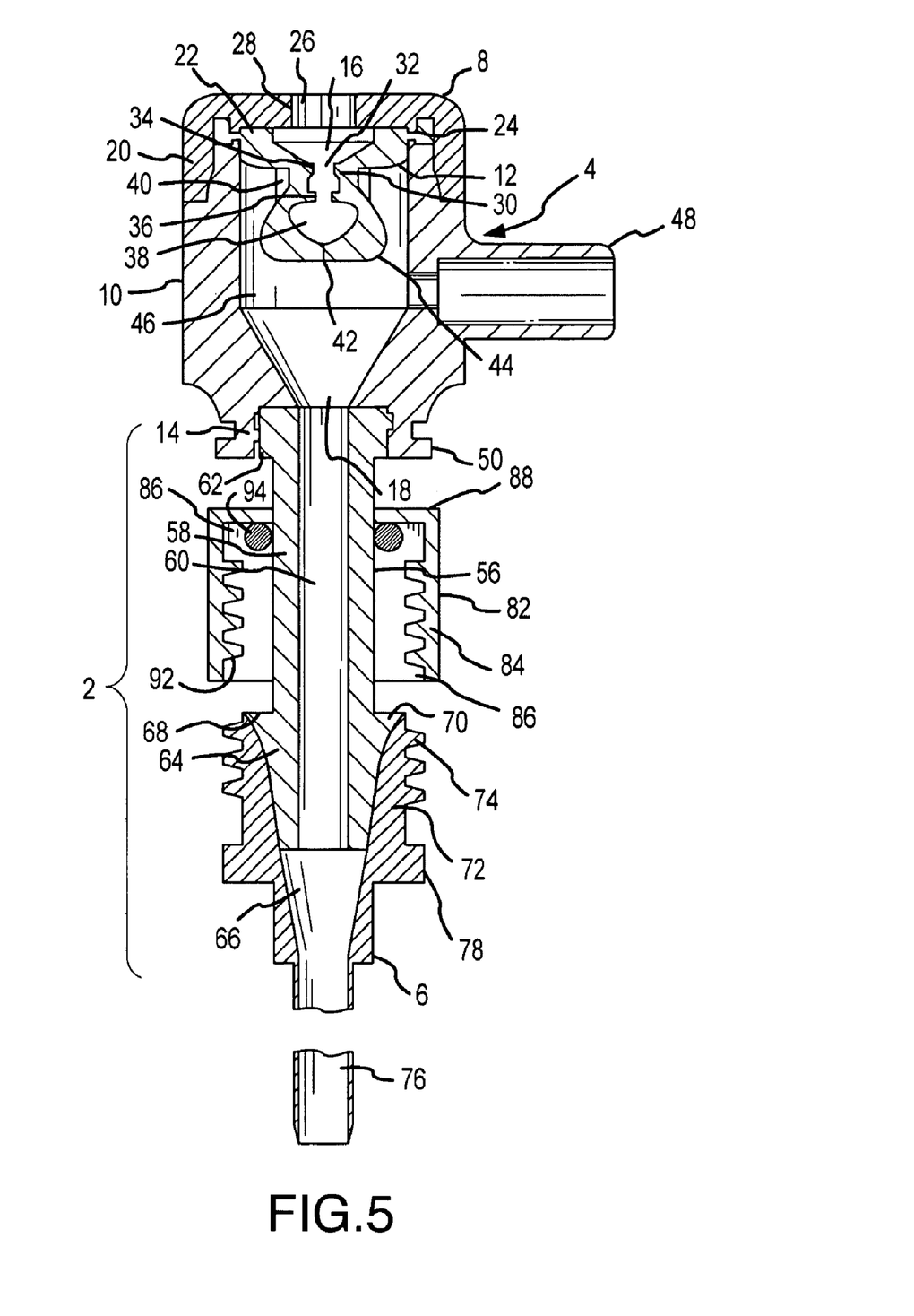
FIG. 5 is a cross section of a connection assembly of the type depicted in FIG. 1 with the sliding connector disengaged from the sheath.

The sliding connector 82 further has an engagement structure 92 for engaging an opposing mating component 74 of the nipple 72 on the sheath 6. In the embodiment of FIGS. 1, 4, and 5, the sliding connector 82 may be provided with internal threading 92 on the interior surface of the sliding connector 82 defined by the connector lumen 86. When the cannula portion 64 of the adapter fitting 56 is seated within the nipple lumen 66, the sliding connector 82 may be moved distally along the shaft 58 to cover the interface between the cannula portion 64 and the nipple 72. The internal threading 92 of the sliding connector 82 may then be engaged with the male threading 74 of the nipple 72. By rotating the sliding connector 82 about the cannula potion 64 and the threading 74 of the nipple 72, the sliding connector 82 may be tightened against the annular shelf 68 of the cannula portion 64. In one embodiment, an elastomeric O-ring 94 may be positioned within the sliding connector 82 to interface between the annular lip 88 and the annular shelf 68 of the cannula portion 64 to create a fluid-tight seal between the adapter fitting 56, the sliding connector 82, and the nipple 72.

By tightening the sliding connector 82 on the nipple 72 of the splittable sheath 6 to a first level of engagement, i.e., until the internal annular lip 88 of the sliding connector 82 seats firmly against the intervening O-ring 94 (causing a slight deformation) and the annular shelf 68 of the cannula portion 64 (as shown in FIG. 2), a fluid seal between the sliding connector 82, the adapter fitting 56 and the splittable sheath 6 is achieved. In addition, if the sliding connector 82 is tightened further to a second level of engagement (see FIG. 4) with the nipple 72, further deforming or flattening the O-ring 94, the wedge 70 is driven distally into the nipple 72. If the wedge 72 is aligned with the weakened or scored portion 80 of the splittable sheath 6, the wedge 70 will initiate separation of the splittable sheath 6 at the second level of engagement. In one embodiment in which the splittable sheath 6 is scored or weakened lengthwise on opposing sides, two wedges 70 may be located on the cannula portion 64 of the adapter fitting 56 180 degrees apart circumferentially in order to interface with each of the weakened portions 80 of the splittable sheath 6. In this manner, separation of the splittable sheath 6 is initiated on both sides when the sliding connector 82 is tightened to a second level of engagement.

In one method of operation utilizing the embodiment of FIGS. 1-5, a needle is inserted into a patient's blood vessel. A guide wire is threaded through the lumen of the needle into the vessel. The needle is then removed leaving the guide wire in the vessel with a portion exposed. A dilator and splittable sheath 6 are then advanced together over the guide wire into the vessel. The dilator tip, which is tapered, increases the size of the opening in the blood vessel as it enters the vessel so that ultimately an opening large enough to accommodate the sheath 6 is formed. After the sheath 6 is inserted into the blood vessel, the dilator and guidewire are removed. The distal end of a medical device, such as a pacemaker lead 90, is then advanced through the splittable sheath 6, into the location within the patient for its utilization.

The hemostasis valve 4, depending upon the type (e.g., single or "universal" diameter) may be attached to the adapter fitting 56, which in turn connects with the sheath 6, at any time during the medical procedure, before or after the lead 90 is placed in the sheath 6. With the hemostasis valve 4 in place, it is possible to insert leads 90 having a wide range of diameters with ease. A lead 90 may be inserted through the first opening in the cap 8 and into the valve assembly 12. If the lead 90 is inserted slightly off center, it will be guided to the neck opening 32 by means of the conical receiving area 28. The lead 90 may then be moved through the passageway of the sealing neck 30 into the semi-spherical sealing chamber 38 and out through the sealing lips 44. After exiting through the sealing lips 44, the lead 90 is advanced through the engagement portion 14, out the opening, through the adapter fitting 56, down through the sheath 6, and into the blood vessel. Any blood that flows between the sheath 6 and the lead 90 and up into the interior of the valve chamber 46 is not permitted to escape to the exterior because of the sealing action of the narrowed portion or portions of the sealing neck 30 around the body of the lead 90 and further due to the sealing action of the O-ring 94 between the sliding connector 82 and the sheath 6.

Alternatively, if a lead 90 is in place, the adapter fitting 56 and the hemostasis valve 4 may be placed over the lead 90. The cannula portion 64 of the adapter fitting 56 may be inserted into the lumen 66 of the nipple 72 extending proximally from the sheath 6 and secured to the nipple 72 by the sliding connector 82. The hemostasis valve 4 may then be then secured onto proximal end of the adapter fitting 56 by rotating it such that the internal threads 14 of the hemostasis valve 4 engage the external threads 62 of the shaft 58. In this manner, the sliding connector 82 can be tightened against the nipple 72 to a first level of engagement, i.e., until the internal annular lip 88 of the sliding connector 82 seats firmly against the intervening O-ring 94 and the annular shelf 68 of the cannula portion 64 (as shown in FIG. 2), thereby creating a fluid tight seal between the adapter fitting 56 and the splittable sheath 6.

When it is time for the physician to remove the hemostasis valve 4, the physician may first tighten the sliding connector 82 to the second level of engagement, i.e., to the point that the wedges 70 are driven into the nipple 72 and separation of the splittable sheath 6 is initiated (as shown in FIG. 4). The physician may then disengage the sliding connector 82 from the nipple 72 by rotating the sliding connector 82 in the opposite direction than the direction used for engaging and securing the sliding connector 82 to the splittable sheath 6. Once disengaged, the sliding connector 82 may then be moved proximally, axially along the shaft 58 of the adapter fitting 56 to reveal the nipple 72 of the splittable sheath 6, as shown in FIG. 5. The physician can then grasp the handle members 78*a*, 78*b* of the sheath 6 and continue separating the sheath 6 with less force than would be needed to initiate the separation of the splittable sheath 6 by tearing. In this manner the possibility of moving or dislodging the lead 90 is lessened because of the smaller tearing force required. The physician can then grasp the exposed section of the lead 90 between his fingers or with an instrument and hold the lead steady while removing the hemostasis valve 40.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A medical instrument introduction system, comprising:
   a hemostasis valve having a first engagement means disposed on a distal end thereof;
   a splittable sheath defining a lumen and having a second engagement means disposed on a proximal end thereof; and
   an adapter fitting comprising:
      a shaft defining a lumen, the shaft having a proximal end and a distal end;
      a third engagement means on an external surface of the proximal end of the shaft for engagement with the first engagement means of the hemostasis valve;
      a cannula portion forming the distal end of the shaft for interfacing with the lumen of the splittable sheath, wherein the lumen is adapted to receive the cannula portion;
      at least one wedge disposed on an external surface of the cannula portion for interfacing with a weakened portion of the splittable sheath; and
   a sliding connector slidably disposed about the shaft of the adapter fitting, the sliding connector defining an opening through which the proximal end of the shaft protrudes, the sliding connector further comprising a fourth engagement means for engagement with the second engagement means of the splittable sheath.

2. The system of claim 1, wherein the splittable sheath further comprises a nipple extending proximally therefrom and wherein the second engagement means is disposed upon the nipple.

3. The system of claim 1 further comprising a sealing means that interfaces between an interior surface of the sliding connector and a proximal surface of the cannula portion of the adapter fitting.

4. The system of claim 1, wherein the at least one wedge comprises two wedges located on 180° apart about an outer surface of the cannula portion of the adapter fitting.

5. The system of claim 2, wherein the at least one wedge comprises two wedges located on 180° apart about an outer surface of the cannula portion of the adapter fitting; and
   wherein each of the two wedges interfaces with an opposing weakened portion of the nipple.

6. The system of claim 3, wherein the interface between the fourth engagement means of the sliding connector, the sealing means, and the second engagement means of the splittable sheath provides for a first level of engagement resulting in a fluid seal between sliding connector, the adapter fitting, and the splittable sheath and further provides for a second level of engagement wherein the at least one wedge initiates separation of the splittable sheath.

7. A medical instrument introduction system, comprising:
   a hemostasis valve having an internally threaded exit lumen disposed on a distal end thereof;

a splittable sheath having an externally threaded nipple disposed on a proximal end thereof; and an adapter fitting comprising:
- a shaft defining a lumen, the shaft having a proximal end and a distal end;
- threading on an external surface of the proximal end of the shaft for engagement with the internally threaded exit lumen of the hemostasis valve;
- a cannula portion forming the distal end of the shaft for interfacing with the splittable sheath;
- at least one wedge disposed on an external surface of the cannula portion for interfacing with a weakened portion of the splittable sheath; and
- a sliding connector slidably disposed about the shaft of the adapter fitting, the sliding connector defining an opening through which the proximal end of the shaft protrudes, the sliding connector further comprising internal threading for engagement with the externally threaded nipple of the splittable sheath.

8. The system of claim 7 further comprising an elastomeric O-ring that interfaces between an interior surface of the sliding connector and a proximal surface of the cannula portion of the adapter fitting.

* * * * *